United States Patent [19]

Nguyen et al.

[11] Patent Number: 5,145,493
[45] Date of Patent: Sep. 8, 1992

[54] MOLECULAR RESTRICTER

[75] Inventors: Hoang K. Nguyen; Joseph M. Draina, both of Austin, Tex.

[73] Assignees: IBM Corporation, Armonk, N.Y.; Motorola Inc., Schaumburg, Ill.

[21] Appl. No.: 722,452

[22] Filed: Jun. 27, 1991

[51] Int. Cl.⁵ .......................................... B01D 57/00
[52] U.S. Cl. ........................................ 55/17; 55/389; 55/521
[58] Field of Search ................. 55/16, 17, 158, 389, 55/521; 138/40–46

[56] References Cited

U.S. PATENT DOCUMENTS

| | | | |
|---|---|---|---|
| 4,466,811 | 8/1984 | Johnson, III | 55/17 |
| 4,764,186 | 8/1988 | Langer | 55/17 |
| 4,770,675 | 9/1988 | Kurzweg et al. | 55/17 X |

FOREIGN PATENT DOCUMENTS 1020960 12/1957 Fed. Rep. of Germany .......... 55/17

Primary Examiner—Robert Spitzer
Attorney, Agent, or Firm—David L. Mossman; James L. Clingan, Jr.; Francis J. Thornton

[57] ABSTRACT

A molecular restricter for inhibiting or preventing gas molecules from flowing past a point, such as a piece of optical equipment, substantially without inhibiting particles mixed therewith from passing therethrough is described. The molecular restricter has a plurality of elongated cells with each end open to permit the particles to pass through. However the width of the cell must be less than the mean free path γ of the molecules under the conditions the restricter is to be used with. In one embodiment, the length of the cell is at least ten times longer than its width. The cells are arranged adjacent to each other and in parallel orientation. The walls of each cell must also be parallel to permit free transmission of the particles or light therethrough.

9 Claims, 3 Drawing Sheets

MOLECULAR RESTRICTER

FIELD OF THE INVENTION

The invention relates to methods and structures for inhibiting or restricting the movement of gas molecules, and, in one aspect, more particularly relates to methods and structures for restricting the movement of gas molecules in system flow streams sufficiently to prevent the molecules from interfering with mechanisms for observing the system, but which does not interfere with other bodies, such as particles, present in the flow stream.

BACKGROUND OF THE INVENTION

It is well known to use equipment having gases, particles, etc. flowing therethrough to accomplish various purposes such as manufacturing, analysis, testing, etc. Additionally it is known to observe such processes by various techniques as a simple window into the equipment, or by sophisticated analytical apparatus. For example, in the manufacture of semiconductors, integrated circuits, and the like, gas flow streams are often used to form layers upon a work piece or substrate, to etch off layers, and the like. These processes are often observed through protective windows. Additionally, in integrated circuit processing it is frequently desirable to monitor the process with an analytical apparatus. One common apparatus is an in situ particle counter which employs a laser beam positioned through the flow pathway. A detector measures the number of particles by sensing light scattering.

A problem with systems using an optical part such as a window or particle counter that depends on good optics for proper functioning is that not only will the gas molecules deposit on the substrate or work piece, they will deposit upon the optical part. Over a relatively short period of time, enough of a deposit is formed to impair vision or to interfere with the operation of the apparatus that requires excellent optics to perform its function.

Thus, there is a need for a way to restrict, inhibit or prevent the molecules from depositing on optical parts without otherwise obstructing the flow. That is, the method should optimally minimize flow restriction of other bodies, such as particles. For example, a device to prevent the transmission of molecules from clouding a particle counter would be useless if it also blocked the particles from coming through.

SUMMARY OF THE INVENTION

Accordingly, it is an object of the present invention to provide a structure for restricting or reducing the number of molecules in a flow stream or pathway.

It is another object of the present invention to provide a mechanism for restricting or reducing the number of molecules in a flow pathway without appreciably reducing the number of particles or other bodies therein.

It is yet another object of the invention to provide a molecular restricter of relatively simple design and low cost.

In carrying out these and other objects of the invention, there is provided, in one form, a molecular restricter for substantially restricting the flow of molecules therethrough having at least one elongated cell with parallel walls and open ends where the cell has a characteristic width, x, representing the distance between the walls within the cell and a length, l. Length l is equal to or greater than x; and x is less than or equal to $\lambda$, where $\lambda$ is the mean free path of the molecules to be restricted. The elongated cells, if more than one is present, are oriented in parallel and are adjacent to each other.

DETAILED DESCRIPTION OF THE INVENTION

Figure 1:
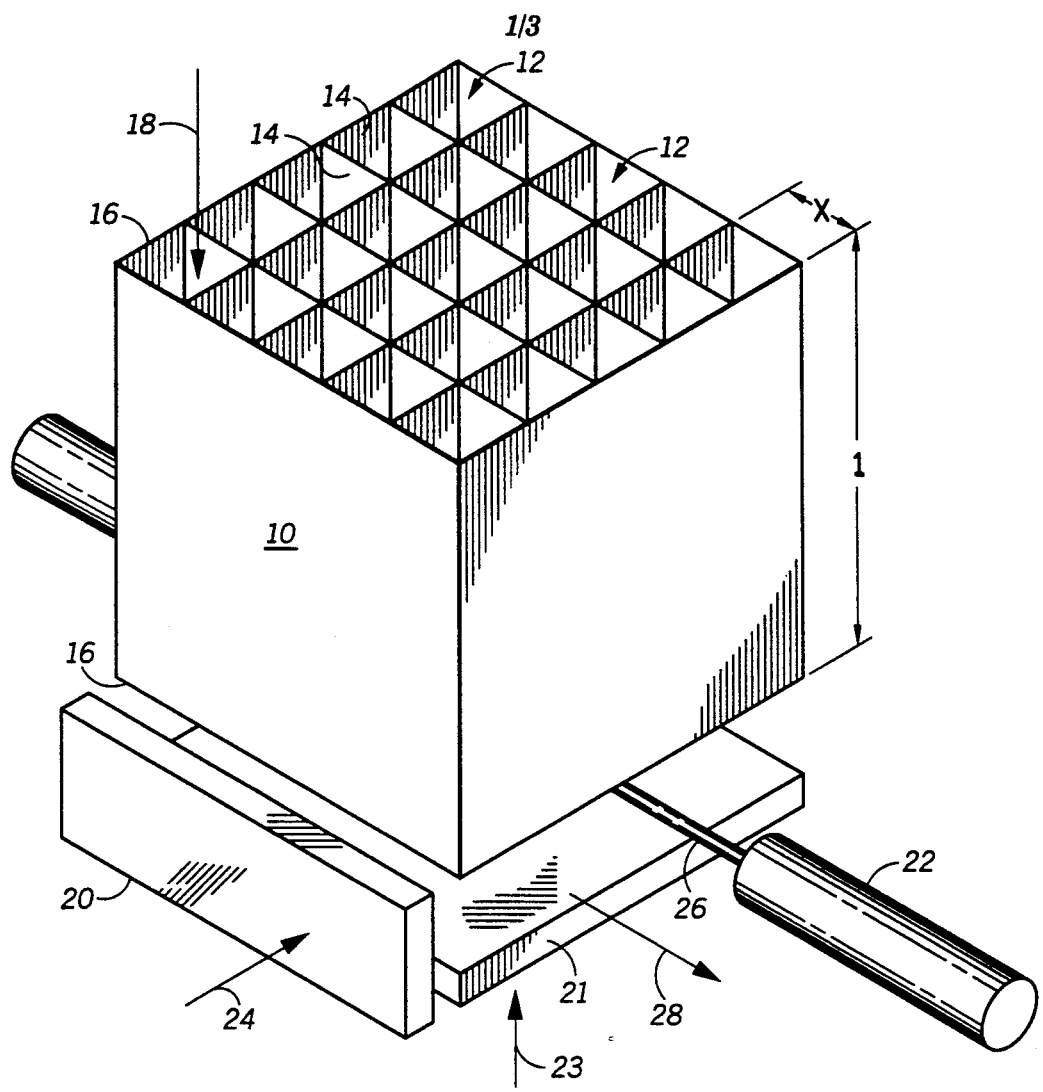
FIG. 1 is a perspective view of one embodiment of a molecular restricter of this invention having cells with square cross-sections positioned relative to some representative optical parts.

Shown in FIG. 1 is the molecular restricter or trap 10 formed from a plurality of elongated cells 12 having parallel walls 14 and open ends 16, where each cell has a characteristic width, x, representing the distance between the walls, and a length l. The cells 12 are oriented in parallel and are adjacent to one another in a packed configuration. Enough cells should be used to have a cross-section that completely covers the flow pathway of the gas molecule and particle stream, which in FIG. 1 is taken to proceed in the direction of arrow 18.

Mechanisms for observing the flow pathway are schematically illustrated in approximate relative position by observation window 20 and particle counter 22. Observations of the interior of a system in which molecular restricter 10 is present is made through first observation window 20 by observing in the direction of arrow 24. Observations may also be made through second observation window 21 observing in the direction of arrow 23. Particle counter 22 analyzes the light scattering from laser beam 26 coming from the direction of arrow 28. While arrows 24 and 28 and the directions represented thereby are at right angles to the direction of the flow pathway 18, this is not required in many systems, though it may be convenient for the system to be set up in this way. The paths of observance, represented by arrows 23, 24 and 28, must intersect the flow pathway represented by arrow 18, but are not necessarily required to be perpendicular thereto. Indeed, the paths of observance may observe directly into the direction of arrow 18. Note that second window 21 is normal to flow pathway 18. Such an orientation may be desirable to observe through the restricter 10, for example to observe or take information from an integrated circuit wafer (not shown) on the other side of the restricter 10. Also, the optical parts, namely window 20 and particle counter 22 may not be directly in the pathway of the flowing gas molecules and particles demonstrated by arrow 18. While it is possible that some analytical equipment might need to be in the pathway, this invention is primarily, but certainly not exclusively, directed to situations where it is desirable to avoid deposition of the gas molecules on the optical parts. Window 20 and counter 22 are simply representative of such parts and the invention is not limited to these apparatus which are simply used for the sake of illustration herein. For example, the restricter 10 could be used as an "anti-window-clouding" device for optical spectrum analyses of plasma, e.g.; for end-point detection device and the like, since the restricter 10 permits light to pass through it. These and other devices are encompassed under the term "optical parts" to be protected by the molecular restricter 10. Note that the molecular restricter 10 must be placed upstream of the optical parts to restrict the gas molecules from approaching these parts.

Figure 2:
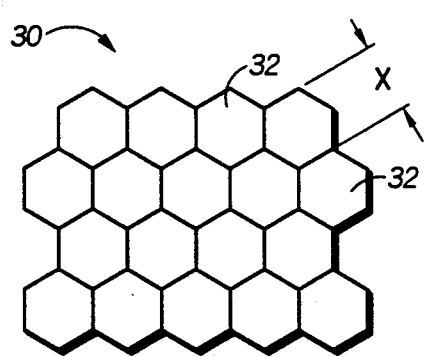
FIG. 2 is a cross-sectional view of an alternate molecular restricter of this invention where the cross-sectional shape of the cells is hexagonal.
Figure 3:
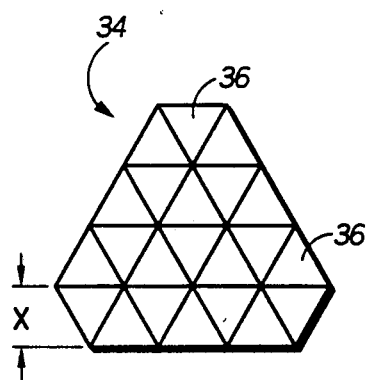
FIG. 3 is a cross-sectional view of an alternate molecular restricter of this invention where the cross-sectional shape of the cells is triangular.

Cells 12 have a cross-sectional shape in FIG. 1 of squares, but this shape is not required to be squares. For example, FIG. 2 is a cross-sectional representation of a molecular restricter 30 where the cells 32 have the cross-sectional shape of hexagons and FIG. 3 is a cross-sectional view of a molecular restricter 34 where the cells 36 have a cross-sectional shape of triangles. These hexagons and triangles need not be regular, i.e. with angles and sides that are equal. Circles, rectangles, trapezoids, rhomboids, etc. may also be used as the cross-sectional shape of the cells. Any shape may be used as long as it may be closely packed together and the cells may be oriented adjacent and parallel to each other. Thus, when viewing through the molecular restricter 10 in the direction of arrow 18, the path through each cell should be open and the cell walls 14 should be viewed only edge on as seen in FIGS. 2 and 3.

The design objective of the molecular restricter or trap 10 is to minimize the amount of gas molecules passing through it and yet allow particulates to pass therethrough. The restricter avoids unwanted depositions of films or reactions which occur at or on optical parts of in situ sensors and view windows. The molecular restricter 10 must be designed at a molecular flow regime with a configuration that minimizes the transmittance of molecules. To achieve this, the mean free path, $\lambda$, that can be expected under the operating conditions is calculated according to equation (1) derived from the kinetic theory of gases:

$$\lambda = \frac{kT}{P\pi\sigma^2 \sqrt{2}} \quad (1)$$

where k is Boltzmann's constant ($1.38066 \times 10^{-23}$ J·K$^{-1}$), T is the temperature of the flow where the molecular restricter 10 is to be used and hence the temperature of the gas, P is the pressure of the gas where the molecular restricter 10 is to be engaging, and $\sigma$ is the molecular diameter of the molecules to be restricted. For example, at 10 mtorr, 22° C. for oxygen, $\lambda$ is 0.5 cm. As the temperature is increased, which is more likely in the presence of reactor systems, $\lambda$ becomes smaller and the restricter becomes more effective.

At room temperature (22° C.) and for a typical molecular diameter of 3 Å:

$$\lambda = \frac{1.455}{P(Pa)} \text{ cm}$$

At very low pressure such as $P \leq 10^{-1}$ Pa or $10^{-3}$ torr, $\lambda$ is large and line-of-sight deposition occurs. The gas molecules would travel straight through the molecular restricter or trap 10 untouched. The molecular restricter 10 should be designed such that the protected optical parts are off from the line-of-sight paths through the restricter 10, as mentioned. The molecular restricter 10 is expected to find its greatest utility in low pressure systems.

To have molecular flow, the Knudsen number ($K_n$) must be greater than 1.0 according to equation (2):

$$K_n = \frac{\lambda}{x} >> 1 \quad (2)$$

where x is the minimum cross-sectional distance perpendicular to the flow path, also called the characteristic dimension. In a circular pipe, x is the diameter; in a conduit of square cross-section, x is the width of a side; generally x is the characteristic width of one cell. At $K_n > 1$, the molecular flow regime begins. In this flow regime, the gas-wall collisions predominate. That is, each molecule arrives, adheres and reemits in a direction independent of its incident velocity. Thus, there is a probability that a molecule entering the pipe with $\lambda > x$ will not be transmitted through, but will be returned to the entrance. Solving for x gives:

$x \leq K_n\lambda = (1.0)(0.5 \text{ cm}) = 0.5 \text{ cm}$

Since $K_n$ should equal 1, x can be taken to be equal to or less than $\lambda$ for this invention. It should be apparent that as x is reduced from the value of $\lambda$ that the amount of molecules transmitted through the trap will diminish.

As noted, the molecular restricter 10 will also become more effective at higher temperatures. For example, in the situation given above as an example only where P=10 mtorr and oxygen is the molecule to be blocked, $\lambda$ was calculated to be 0.5 cm. From the equations, this dimension which provides x and l will increase making the molecular restricter 10 more effective at higher temperatures. In one non-limiting example, this restricter with x=0.5 cm would be effective for temperatures of 22° C. to 1,000° C. and beyond.

It will be appreciated that the exact geometry of the cells and the molecular restricter in which they reside should be optimized for each situation or system as there are a number of factors to be considered in determining the desired geometries. A proposed geometry is a square cross-sectional pass through with a length of l at least equal to or greater than x. It is preferred, in one aspect, that l is greater than x. In one embodiment of the invention, l is equal to or greater than 2.5x. Increased restricting is provided at a preferred embodiment of l being equal to or greater than 5.0x. In a most preferred aspect, l is greater than or equal to 10x to greatly reduce the probability of gas molecules passing through. At this length the transmission probability is approximately 13 percent. Thus, length l in some cases is at least 10x or greater. At greater lengths, the transmission probability approaches zero, with a point of diminishing returns reached shortly after a length of 10x. Thus, while lengths l greater than 10x may be desirable to reduce the transmission probability to near zero in some instances, in most cases space limitations and diminishing returns will limit l to 1x to 20x, or more preferably from about 2.5x to 15x.

An alternative would be to increase the effective length of l by decreasing x, that is, make the cell cross-sections smaller. This approach, too, would reach diminishing returns since the thicknesses of the cell walls would begin to span an appreciable part of the flow path and particles would begin being blocked, which is not desirable. For example only, one minimum dimension for x could be as small as about 0.1 cm (0.035"), when oxygen is the molecule being blocked, where the pressure is about 50 mtorr and the temperature is 22° C., although the invention is not limited to this suggested dimension. It is again emphasized that the 1/x ratio, sometimes called the aspect ratio, should be optimized for each application to allow maximum transmission of light and/or particles, if needed, and minimum transmission of molecules, if needed. Physical space considerations enter into the optimization as well.

In addition, with this design and at low operating pressure (approximately 1 to 10 mtorr, for instance) the mean free path λ is the same or longer than the cross-sectional diameter. Because of the long mean free path only the molecules (of the 13 percent remaining) that travel parallel with the longitudinal axis of the restricter 10 will pass through the trap. Since the molecules travel straight through, they will not affect the optics or windows located down stream of the restricter or trap 10 as shown in FIG. 1.

The molecular restricter need not be made out of any special material, as long as it is compatible with the reactions being conducted in the system. For example, if the restricter is used in an etcher, it should not be of a material that is easily etched by the reaction of importance. However, it may be made of metal, including, but not limited to aluminum; organic polymers and the like; and should be inert and electrically neutral.

The invention will be illustrated further with respect to the following examples which are not intended to limit the scope of the invention.

EXAMPLES 1-2

A molecular restricter of cells with circular cross-sections was used in a High Yield Technology (HYT) in situ particle counter experiment with and without the restricter separately at 1 atm pressure conditions. The restricter used with the HYT sensor had x=0.4 cm and l=3.3 cm to give an aspect ratio of 8.25. It will be appreciated that the restricter may be used with other systems and in conjunction with other materials besides $SiO_2$ which is employed herein as an illustrative example only. Two runs were conducted with the restricter (Ex. 1) as shown. The following results were obtained:

TABLE I

| Measurements With and Without Restricter in Place | | |
|---|---|---|
| Parameter | Example 1 With Restricter | Example 2 Without Restricter |
| Particle counts | 38.8 | 40.1 |
| $SiO_2$ film deposition, total, Å | 40/720 | 47,800 |
| Transmission ratio, % | 0.3/1.5 | 100 |
| Aspect ratio l/x | 20/10 | — |

It may be seen from Table I that the presence of the molecular restricter does limit the number of molecules passing therethrough and thus in front of the particle counter. The number of molecules transmitted is proportional to the $SiO_2$ thickness measured, and the thickness decreased from 47,800Å to 40Å resulting in only a 0.3% transmission through the restricter with aspect ratio 1/x=20. Yet it may be seen that the particle counts of 38.8 and 40.1 roughly agree indicating little or no effect on the transmission of particles. As noted, the restricter will work best at low pressure where $K_n$ is about 1 or greater and the molecular theory of gases holds.

Figures 4A, 4B:
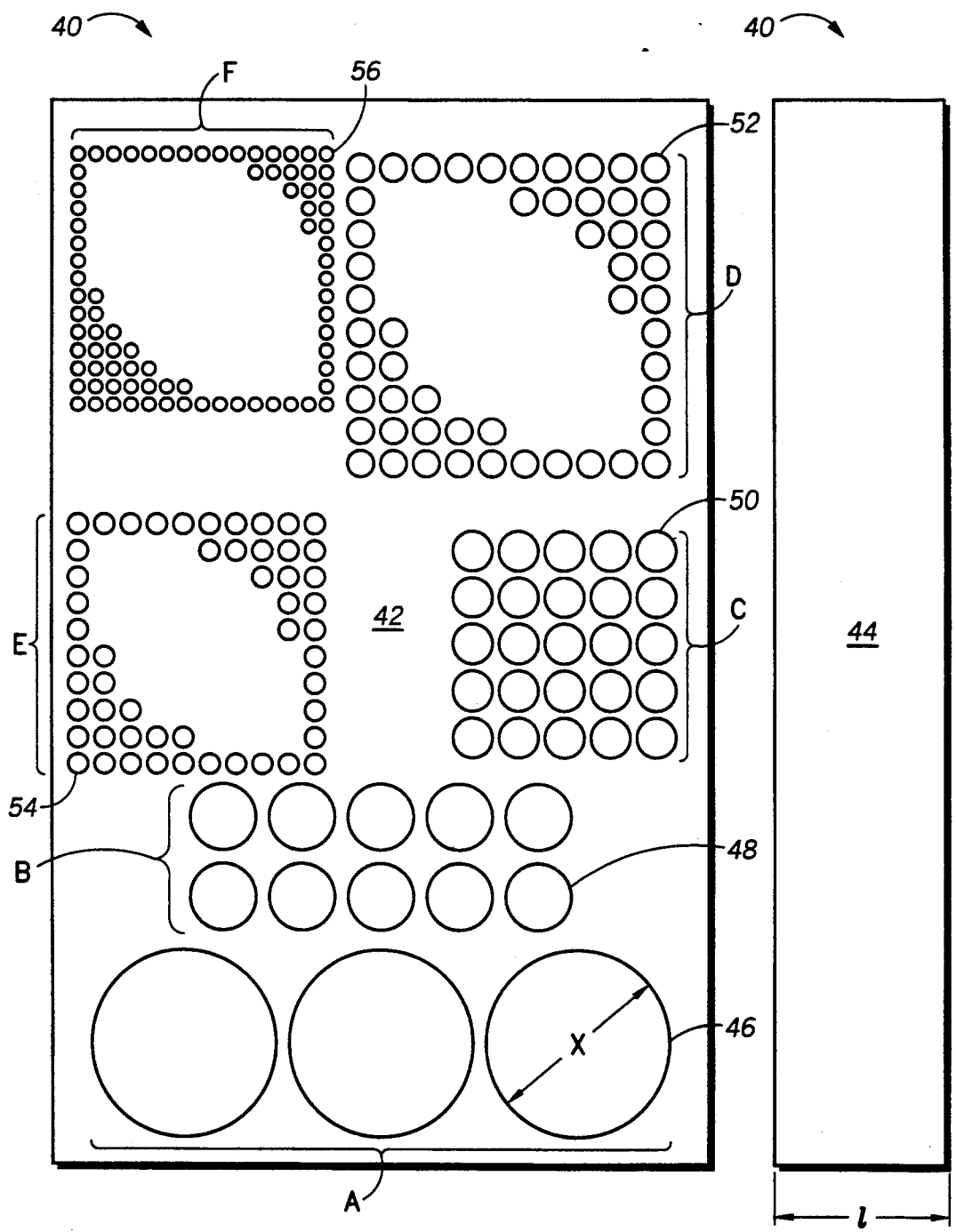
FIG. 4A is a plan view of one embodiment of the molecular restricter of the invention having six arrays of variously sized cells which was used as a test vehicle.
FIG. 4B is a side view of the molecular restricter of FIG. 4A to scale therewith.
Figure 5:
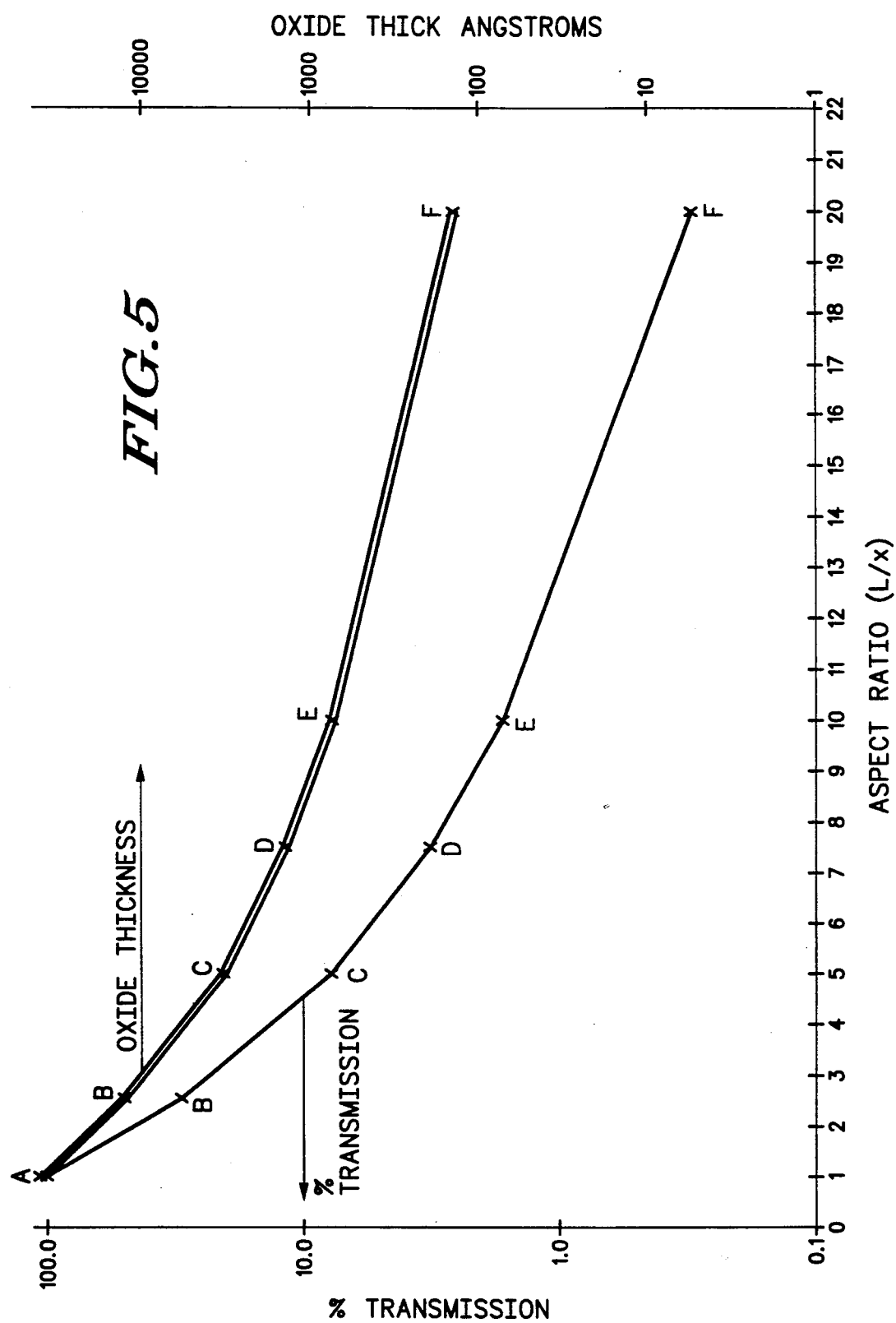
FIG. 5 shows plots of the molecular transmission of oxygen molecules and silicon dioxide deposition thicknesses as a function of the geometry or aspect ratio of the various arrays of the molecular restricter of FIGS. 4A and 4B.

FIGS. 4A and 4B shown front and side views, respectively, of a molecular restricter 40 having six different arrays, A-F, of variously sized cells that was built of 6061 aluminum and positioned directly on a wafer to obtain the molecular transmission data and silicon dioxide deposition data given in FIG. 5. Molecular restricter 40 has a front face 42 and a side face 44, and is represented approximately twice actual size for clarity. FIG. 4B is to the scale of 4A, and represents l to be 0.7" (1.78 cm) thick. In arrays D, E and F the number of cells 52, 54 and 56, respectively, are only partially represented. The dimensions x and other information for the various cells or holes are given in Table II.

TABLE II

| Dimensions of Cells in Molecular Restricter 40 | | | | |
|---|---|---|---|---|
| Array | Cell ref. no. | Diameter x, in./(cm) | Aspect ratio, l/x | Cell arrangement | No. of cells in array |
| A | 46 | 0.7/(1.78) | 1 | 1 × 3 | 3 |
| B | 48 | 0.280/(0.71) | 2.5 | 2 × 5 | 10 |
| C | 50 | 0.140/(0.35) | 5 | 5 × 5 | 25 |
| D | 52 | 0.095/(0.24) | 7.4 | 10 × 10 | 100 |
| E | 54 | 0.070/(0.18) | 10 | 10 × 10 | 100 |
| F | 56 | 0.035/(0.09) | 20 | 15 × 15 | 225 |

In a non-limiting example, the spacing between the cell or hole edges may vary from 10 to 40 mils apart within the same cell size groups or arrays. It is noted that the spacing between the arrays or groups could be much larger than that represented in FIG. 4A. Also, it will be appreciated that the geometric arrangement of the circular cells 46-46 of molecular restricter 40 could be more compactly arranged in a hexagonal configuration, rather than the square grid shown in FIG. 4A. Such an arrangement would help minimize the amount of material (e.g. aluminum) between the cells that might potentially block particles or light.

EXAMPLE A-F

Molecular restricter 40 was positioned over a test silicon wafer and effluents from a silane/$O_2$ plasma discharge was flowed through the system chamber containing the wafer and the restricter 40 at a pressure of 2.5 mtorr and a temperature of 22° C. The percent transmission and silicon dioxide thickness in Angstroms were measured for each array which corresponds to each Example, which are plotted in FIG. 5. It can be clearly seen that as the aspect ratio, 1/x increases from array A to array F that the transmission of molecules decreases, as does the amount of $SiO_2$, though not as sharply as does the molecular transmission.

Thus, the molecular restricter is quite effective. At an aspect ratio of 2/1, the molecular transmission is about half of that where it is 1/1. At a ratio of 5/1, only about 9% is transmitted, on down to about 1% transmitted at a ratio of only about 12.5/1.

At some point the molecular restricter would have to be removed for cleaning as the film is deposited over the entrance to reduce the danger of this layer being fragmented or sputtered off.

Many modifications may be made in the structure and method of the present invention without departing from the scope thereof. For example, the molecular restricter could be installed on in situ particle counters such as High Yield Technology or Applied Materials counters for use in low pressure chemical vapor deposition (CVD), sputtering and etching systems. The restricter may also be installed on view windows or view ports to prevent film coating problems that could degrade optical quality of the window or port. Further, a removable honeycomb structure to fit the reactor wall so that the film-forming reaction would not take place at the reactor wall, but on the honeycomb structure which could be made removable at regular intervals for cleaning. As noted earlier, the cross-sectional shape of the individual cells may be different shapes than those shown and described herein.

I claim:

1. In a system having a mixed flow of gas molecules and particles, a method for restricting the flow of gas molecules without substantially restricting the flow of particles therethrough comprising:
   providing a means for flowing gas molecules and particles in a first direction along a pathway;
   providing means for observing the particles in a second direction, where the second direction is not parallel to the first direction;
   installing a molecular restricter in the pathway upstream from the means for observing, for substantially restricting the flow of molecules therethrough, the molecular restricter comprising:
   a plurality of elongated cells having parallel walls and open ends where the cells has a characteristic width, x, representing the distance between the walls within the cell and a length, l;
   where l is equal to or greater than x;
   where x is less than or equal to $\lambda$, where $\lambda$ is the means free path of the molecules; and
   where the elongated cells are oriented in parallel and adjacent to each other.

2. The method of claim 1 where the mean free path $\lambda$ of the molecules is determined by the formula:

$$\lambda = \frac{kT}{P\pi\sigma^2 \sqrt{2}}$$

where k is Boltzmann's constant, T is the temperature where the molecular restricter is to be used, P is the pressure where the molecular restricter is to be used, and $\sigma$ is the molecular diameter of the molecules to be restricted.

3. The method of claim where the cells of the molecular restricter have a cross-sectional shape which is selected from the group consisting of squares, rectangles, hexagons, triangles and circles.

4. A molecular restricter for substantially restricting the flow of molecules therethrough comprising:
   at least one elongated cell having parallel walls and open ends where the cell has a characteristic width, x, representing the distance between the walls within the cell and a length, l;
   where l is equal to or greater than x;
   where x is less than or equal to $\lambda$, where $\lambda$ is the mean free pathway of the molecules; and
   where each of the at least one elongated cells are oriented in parallel and adjacent to each other when more than one cell is present.

5. The molecular restricter of claim 4 where the mean free path $\lambda$ is determined by the formula:

$$\lambda = \frac{kT}{P\pi\sigma^2 \sqrt{2}}$$

where k is Boltzmann's constant, T is the temperature where the molecular restricter is to be used, P is the pressure where the molecular restricter is to be used, and $\sigma$ is the molecular diameter of the molecules to be restricted.

6. The molecular restricter of claim 4 where the cells have a cross-sectional shape which is selected from the group consisting of squares, retangles, hexagons, triangles and circles.

7. An improved system comprising:
   means for flowing gas molecules and particles in a first direction along a pathway;
   means for observing the particles in a second direction, where the second direction is not parallel to the first direction;
   the improvement comprising a molecular restricter in the pathway upstream from the means for observing, for substantially restricting the flow of molecules therethrough, the molecular restricter comprising:
   at least one elongated cell having parallel walls and open ends where the cell has a characteristic width, x, representing the distance between the walls within the cell and a length, l;
   where l is equal to or greater than x;
   where x is less than or equal to $\lambda$, where $\lambda$ is the mean free path of the molecules; and
   where each of the at least one elongated cells are oriented in parallel and adjacent to each other when more than one cell is present.

8. The improved system of claim 7 where the mean free path $\lambda$ is determined by the formula:

$$\lambda = \frac{kT}{P\pi\sigma^2 \sqrt{2}}$$

where k is Boltzmann's constant, T is the temperature where the molecular restricter is to be used, P is the pressure where the molecular restricter is to be used, and $\sigma$ is the molecular diameter of the molecules to be restricted.

9. The molecular restricter of claim 7 where the cells have a cross-sectional shape which is selected from the group consisting of squares, rectangles, hexagons, triangles and circles.

* * * * *